US00PP16706P2

(12) United States Plant Patent
Michalik

(10) Patent No.: US PP16,706 P2
(45) Date of Patent: Jun. 20, 2006

(54) ***GERANIUM* PLANT NAMED 'PACWHITE'**

(50) Latin Name: *Pelargonium peltatum*
Varietal Denomination: Pacwhite

(75) Inventor: Andrea Michalik, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 51 days.

(21) Appl. No.: 11/073,459

(22) Filed: Mar. 5, 2005

(51) Int. Cl.
*A01H 5/00* (2006.01)

(52) U.S. Cl. ..... Plt./332
(58) Field of Classification Search ..... Plt./332
See application file for complete search history.

*Primary Examiner*—Kent Bell
(74) *Attorney, Agent, or Firm*—C. A. Whealy

(57) ABSTRACT

A new and distinct cultivar of Ivy *Geranium* plant named 'Pacwhite', characterized by its upright, outward spreading and trailing plant habit; vigorous growth habit; freely basal branching habit; large, single and white-colored flowers; and good garden performance.

1 Drawing Sheet

Botanical designation: *Pelargonium peltatum.*
Cultivar denomination: 'Pacwhite'.

CROSS-REFERENCE TO RELATED APPLICATION

The present application is co-pending with the following application: *Geranium* Plant Named 'Pacharl'; Andrea Michalik, applicant.

BACKGROUND OF THE INVENTION

The present invention relates to a new and distinct cultivar of Ivy *Geranium* plant, botanically known as *Pelargonium peltatum*, and hereinafter referred to by the name 'Pacwhite'.

The new Ivy *Geranium* is a product of a planned breeding program conducted by the Inventor in Dresden, Germany. The objective of the breeding program was to develop new large Ivy *Geraniums* with attractive flower coloration.

The new Ivy *Geranium* originated from a cross-pollination made by the Inventor during 2001 of two proprietary selections of *Pelargonium peltatum*, not patented. The cultivar Pacwhite was discovered and selected by the Inventor as a flowering plant within the progeny from the stated cross-pollination in a controlled environment in Dresden, Germany in 2002 .

Asexual reproduction of the new cultivar by terminal cuttings in a controlled environment in Dresden, Germany since 2002 has shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'Pacwhite'. These characteristics in combination distinguish 'Pacwhite' as a new cultivar and distinguish it from other known Ivy *Geranium* cultivars:

1. Upright, outwardly spreading and trailing plant habit.
2. Vigorous growth habit.
3. Freely basal branching habit.

4. Large, single and white-colored flowers.
5. Good garden performance.

Plants of the new Ivy *Geranium* differ primarly from plants of the parent selections in flower coloration.

Plants of the new Ivy *Geranium* can be compared to plants of the cultivar Pacharl, disclosed in U.S. Plant patent application Ser. No. 11/073,468. In side-by-side comparisons conducted in Dresden. Germany, plants of the new Ivy *Geranium* differed from plants of the cultivar Pacharl in the following characteristics:

1. Plants of the new Ivy *Geranium* had longer leaves than plants of the cultivar Pacharl.
2. Plants of the new Ivy *Geranium* were not as freely flowering as plants of the cultivar Pacharl.
3. Flower color of plants of the new Ivy *Geranium* was white whereas flower color of plants of the cultivar Pacharl was scarlet red.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Ivy *Geranium*. The photograph comprises a side perspective view of a typical flowering plant of 'Pacwhite' grown in a container.

DETAILED BOTANICAL DESCRIPTION

Plants of the cultivar Pacwhite have not been observed under all possible environmental conditions. The phenotype may vary somewhat with variations in environment, such as temperature and light intensity, without, however, any variance in genotype.

The aforementioned photograph, following observations and averaged measurements describe plants grown during the spring in containers in Dresden, Germany, and under commercial practice in a glass-covered greenhouse with day temperatures about 18° C., night temperatures about 16° C. and levels less than 60,000 lux. Plants used for the photograph and the description were about four months old. In the following description, color references are made to The Royal Horticultural Society Colour Chart, 1995 Edition, except where general terms of ordinary dictionary significance are used.

Botanical classification: *Pelargonium peltatum* cultivar Pacwhite.

Parentage:

*Female, or seed, parent.*—Proprietary selection of *Pelargonium peltatum*, not patented.

*Male, or pollen, parent.*—Proprietary selection of *Pelargonium peltatum*, not patented.

Propagation:

*Type cutting.*—Terminal cuttings.

*Time to initiate roots.*—Summer: About 10 days at 23° C. Winter: About 12 days at 23° C.

*Time to produce a rooted young plant.*—Summer: About 28 days at 23° C. Winter: About 30 days at 23° C.

*Root description.*—Fine, fibrous; white in color.

*Rooting habit.*—Freely branching, moderately dense.

Plant description:

*General appearance.*—Upright, outwardly spreading and trailing plant habit; uniformly mounded; densely foliated.

*Growth and branching habit.*—Vigorous growth habit. Freely basal branching habit with about seven lateral branches per plant.

*Plant height, to top of umbels.*—About 25 to 28 cm.

*Plant height, to top of foliar plane.*—About 20 cm.

*Plant width.*—About 27 to 30 cm.

*Lateral branches.*—Length: About 18 to 25 cm. Diameter: About 7 mm. Internode length: About 4 to 6 cm. Texture: Slightly pubescent. Color: Close to 144A.

*Foliage description.*—Arrangement: Alternate or opposite; simple. Length: About 6 cm. Width: About 6 cm. Shape: Palmate. Apex: Acute. Base: Cordate; open. Margin: Biserrate. Venation pattern: Palmate. Texture, upper surface: Slightly pubescent; leathery. Texture, lower surface: Smooth, glabrous; leathery. Color: Developing and fully expanded foliage, upper surface: 137A; venation, similar to lamina. Developing and fully expanded foliage, lower surface: 137C; venation, 143B. Zonation pattern: Intensity: Weak. Location of zone from margin: About 2 cm. Width: About 2 cm. Color: 146A. Petiole: Length: About 3 to 4 cm. Diameter: About 2 to 3 mm. Texture, upper and lower surfaces: Pubescent. Color, upper and lower surfaces: Close to 144A.

Flower description:

*Flower arranagement.*—White-colored flowers; single rotate flowers arranged in rounded hemispherical umbels arising from apical leaf axils. Umbels displayed above the foliage on strong peduncles. Flowers face upright to outward; flowers mostly flat. Flowers not persistent. Flowers not fragrant.

*Quantity of flowers.*—About seven flower buds and open flowers per umbel.

*Flowering season.*—Year-round under greenhouse conditions. In the garden in Dresden, Germany, flowering is continuous during the spring and summer.

*Flower longevity.*—Indivdual flowers last about five to seven days on the plant.

*Umbel height.*—About 5.5 cm.

*Umbel diameter.*—About 7 cm.

*Flower diameter.*—About 4.5 cm.

*Flower depth* (*height*).—About 1 cm.

*Flower buds.*—Length: About 1.6 cm. Diameter: About 5 mm. Shape: Elliptic. Color: Close to 144A.

*Petals.*—Quantity per flower: About five. Length: About 3 cm. Width: About 1.8 cm. Shape: Obovate. Apex: Rounded. Base: Attenuate. Margin: Entire. Texture, upper and lower surfaces: Smooth, glabrous; velvety. Color: When opening and fully opened, upper surface: Close to 155D; venation, 74A. When opening and fully opened, lower surface: Close to 155D; venation, 74C.

*Petaloids.*—None observed.

*Sepals.*—Quantity per flower: Five, arranged in a single whorl. Length: About 1.5 cm. Width: About 6 to 7 mm. Shape: Lanceolate. Apex: Acute. Base: Attenuate. Margin: Entire. Texture, upper and lower surfaces: Pubescent. Color, upper and lower surfaces: Close to 144A.

*Peduncle* (*umbel stem*).—Length: About 7 to 8 cm. Diameter: About 2 to 3 mm. Strength: Strong. Texture: Pubescent. Color: Close to 146B.

*Pedicel* (*individual flower stem*).—Length: About 3 cm. Diameter: About 2 mm. Strength: Strong. Texture: Pubescent. Color: Close to 146B.

*Reproductive organs.*—Androecium: Stamen quantity per flower: About seven. Anther length: About 2 mm. Anther shape: Oblong. Anther color: Pink. Pollen amount: Abundant. Pollen color: Orange. Gynoecium: Pistil quantity per flower: One. Pistil length: About 1.1 cm. Stigma shape: Five-parted. Stigma color: Pink. Style length: About 3 mm. Style color: White. Ovary color: Close to 144A.

*Seed.*—Length: About 3 to 4 mm. Diameter: About 1 mm. Shape: Oval. Color: Brown.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind, and temperatures ranging from 5 to 30° C. and have demonstrated good garden performance.

It is claimed:

1. A new and distinct cultivar of Ivy *Geranium* plant named 'Pacwhite', as herein illustrated and described.

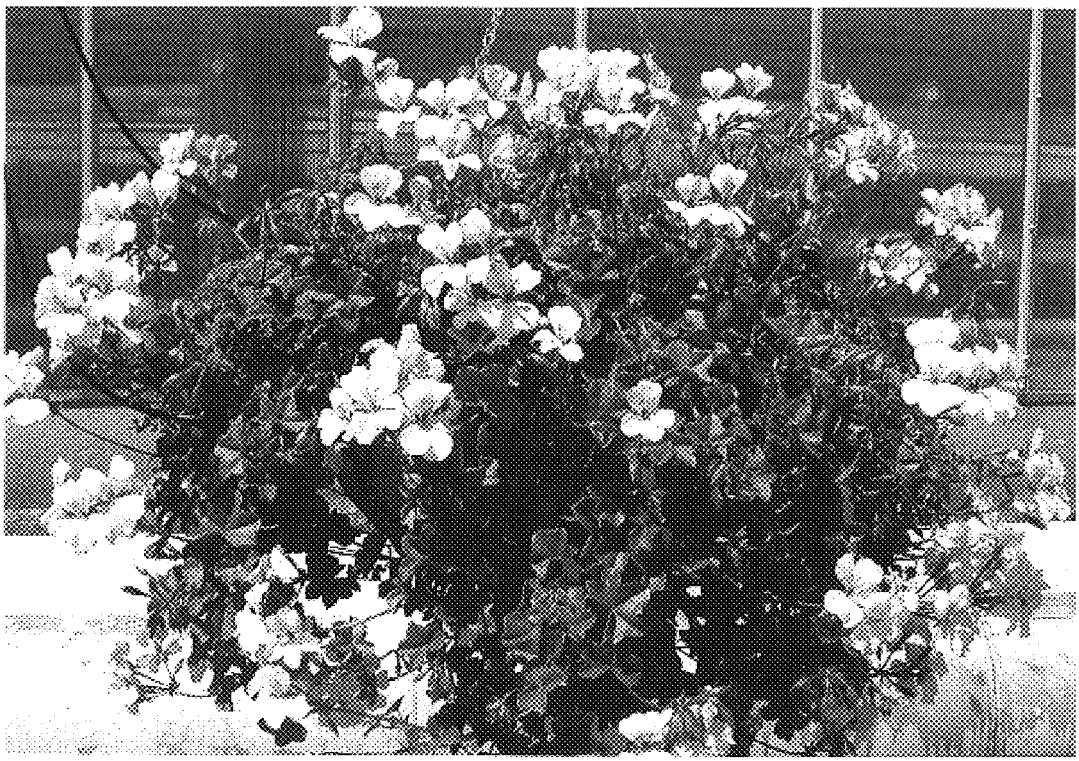

* * * * *